United States Patent
Wang

(10) Patent No.: US 7,717,728 B1
(45) Date of Patent: May 18, 2010

(54) ELECTRICAL CONNECTOR

(75) Inventor: Mei-Hui Wang, Hsin-Tien (TW)

(73) Assignee: Advanced Connectek Inc., Hsin-Tien (TW)

( * ) Notice: Subject to any disclaimer, the term of this patent is extended or adjusted under 35 U.S.C. 154(b) by 0 days.

(21) Appl. No.: 12/404,538

(22) Filed: Mar. 16, 2009

(30) Foreign Application Priority Data

Jan. 15, 2009 (TW) ............................ 98200717 U

(51) Int. Cl.
*H01R 13/62* (2006.01)
(52) U.S. Cl. ........................................ 439/328; 439/83
(58) Field of Classification Search ............ 439/59–62, 439/83, 157, 325–329
See application file for complete search history.

(56) References Cited

U.S. PATENT DOCUMENTS 3,905,665 A * 9/1975 Lynch et al. .................. 439/62
4,761,141 A * 8/1988 Hawk et al. ................. 439/153
5,387,115 A * 2/1995 Kozel et al. ................. 439/157
6,960,093 B1 * 11/2005 Fan ............................. 439/326

* cited by examiner

*Primary Examiner*—Khiem Nguyen
(74) *Attorney, Agent, or Firm*—Alan Kamrath; Kamrath & Associates PA

(57) ABSTRACT

An electrical connector has an insulative housing, terminals and two fastening assemblies. Each fastening assembly has a latching member and a bracket. The latching member is mounted movably on the insulative housing and has a hooking section to hook on a memory module. The bracket is mounted pivotally on the latching member and has a soldering section soldered on a PCB. Because the bracket is pivotally adjustable on the latching member, the electrical connector may be mounted easily on different PCBs with different tolerances.

11 Claims, 9 Drawing Sheets

ELECTRICAL CONNECTOR

BACKGROUND OF THE INVENTION

1. Field of the Invention

The present invention relates to a connector, and more particularly to an electrical connector that has an adjustable fastening assembly so that the electrical connector may be mounted successfully on different printed circuit boards (PCBs) with different tolerances and stably hold a memory module.

2. Description of Related Art

Connectors are general components in electronic devices. For example, a notebook has socket connectors to hold memory modules.

A conventional socket connector for holding memory modules is mounted on a PCB and may hold a memory module. The memory module has two sides and two notches defined respectively in the sides. The socket connector has an insulative housing, a plurality of terminals and two fastening elements. The insulative housing has two opposite sides. The each fastening element has a resilient tab and a bracket. The resilient tabs are mounted respectively on the sides of the insulative housing and each resilient tab has a hooking portion hooking on one notch of the memory module. The brackets are mounted securely on the PCB and respectively abut the resilient tabs to prevent the resilient tabs from irreversibly deforming.

However, the insulative housing, resilient tabs, brackets and PCB are manufactured individually and have different tolerances. Therefore, the resilient tabs are misaligned easily with the brackets when the aforementioned components are assembled so that mounting the brackets on the PCB easily fails. Furthermore, the different tolerances cause shift of the resilient tabs to hinder the installation of a memory module on the socket connector.

To overcome the shortcomings, the present invention provides an electrical connector to mitigate or obviate the aforementioned problems.

SUMMARY OF THE INVENTION

The main objective of the invention is to provide an electrical connector that has an adjustable fastening assembly so that the electrical connector may be mounted successfully on different printed circuit boards (PCBs) with different tolerances and stably hold a memory module.

An electrical connector has an insulative housing, terminals and two fastening assemblies. Each fastening assembly has a latching member and a bracket. The latching member is mounted movably on the insulative housing and has a hooking section to hook on a memory module. The bracket is mounted pivotally on the latching member and has a soldering section soldered on a PCB. Because the bracket is pivotally adjustable on the latching member, the electrical connector may be mounted easily on different PCBs with different tolerances.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
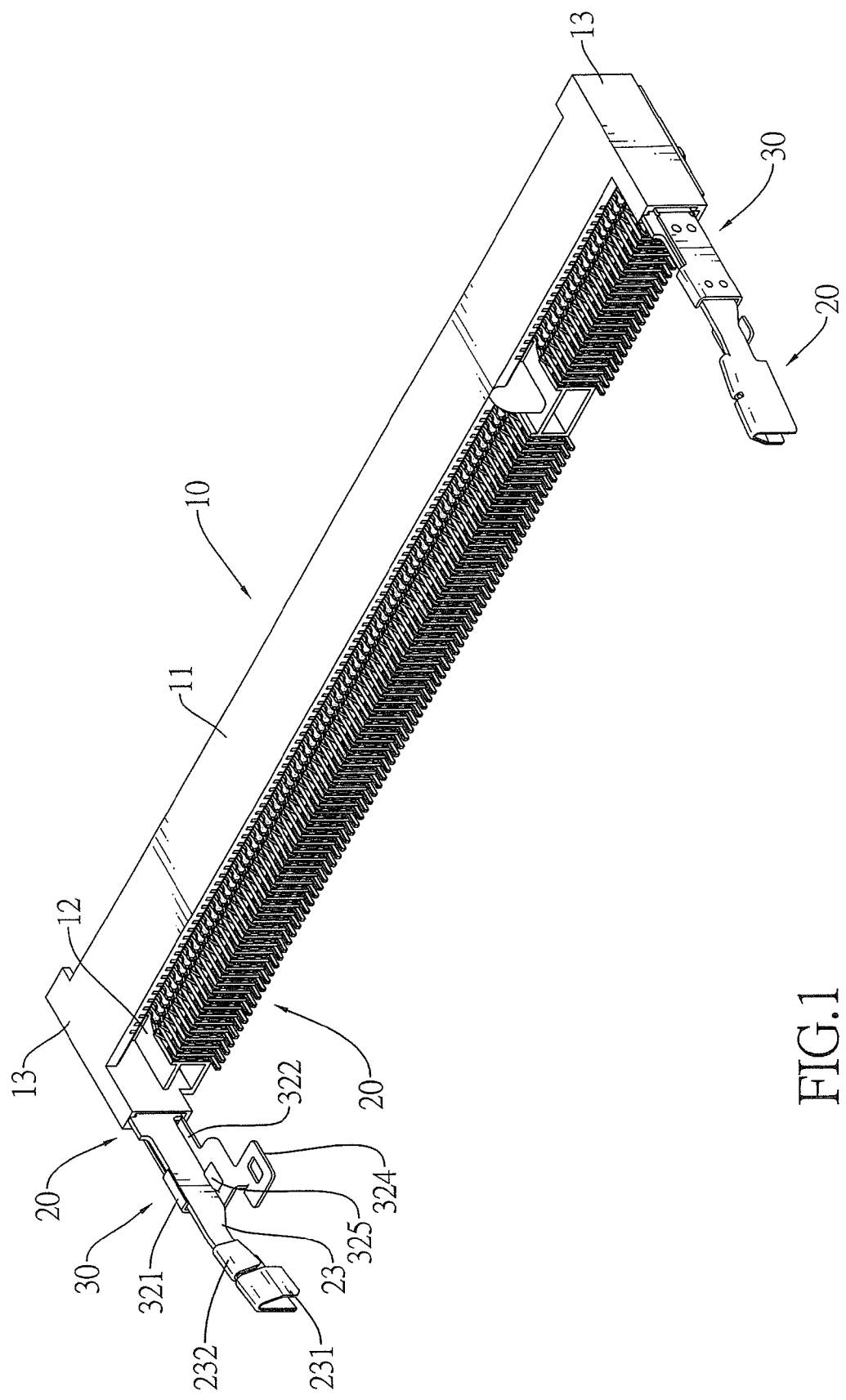
FIG. 1 is a perspective view of an electrical connector in accordance with the present invention.
Figure 2:
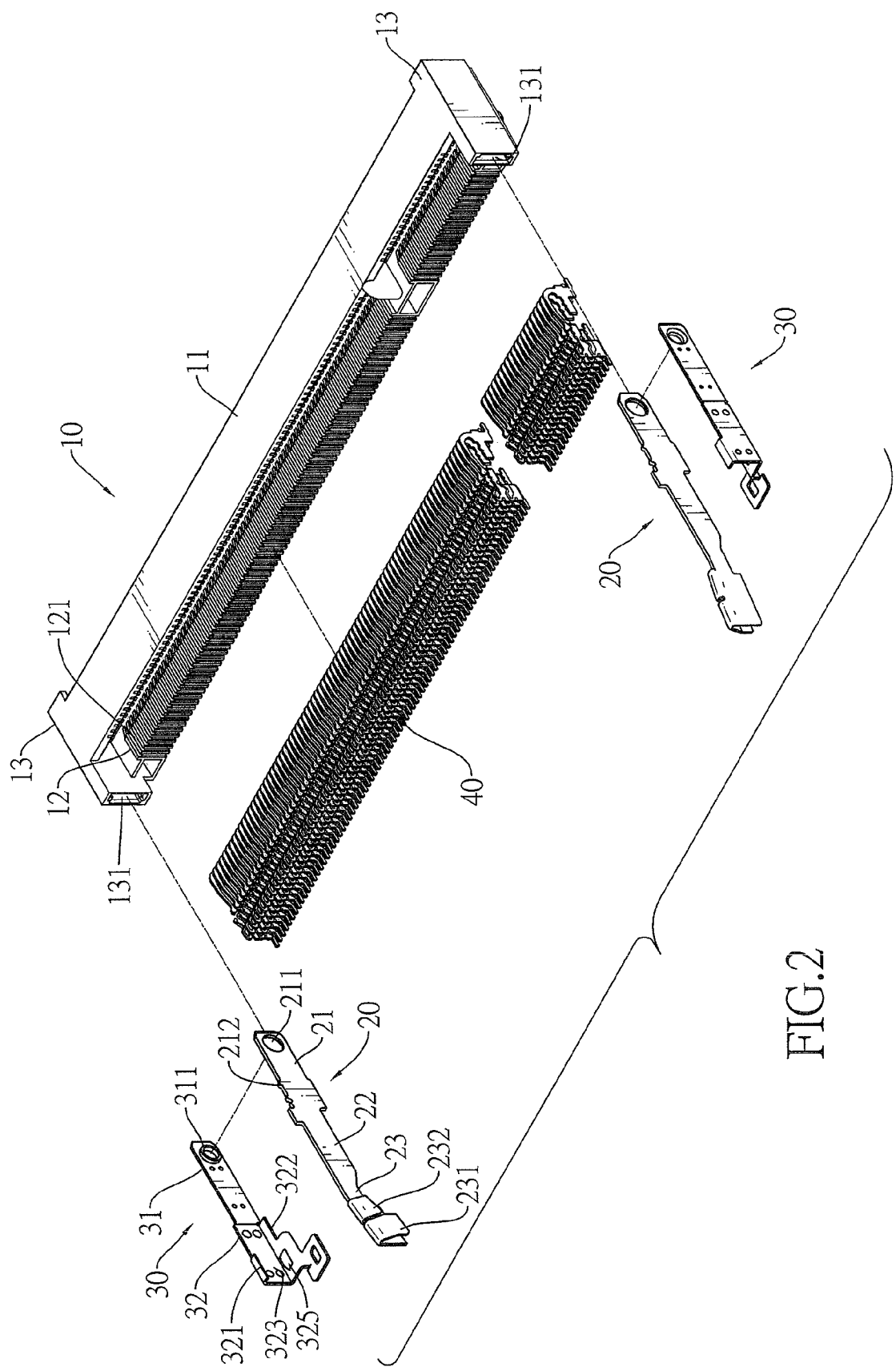
FIG. 2 is an exploded perspective view of the electrical connector in accordance with the present invention.
Figure 3:
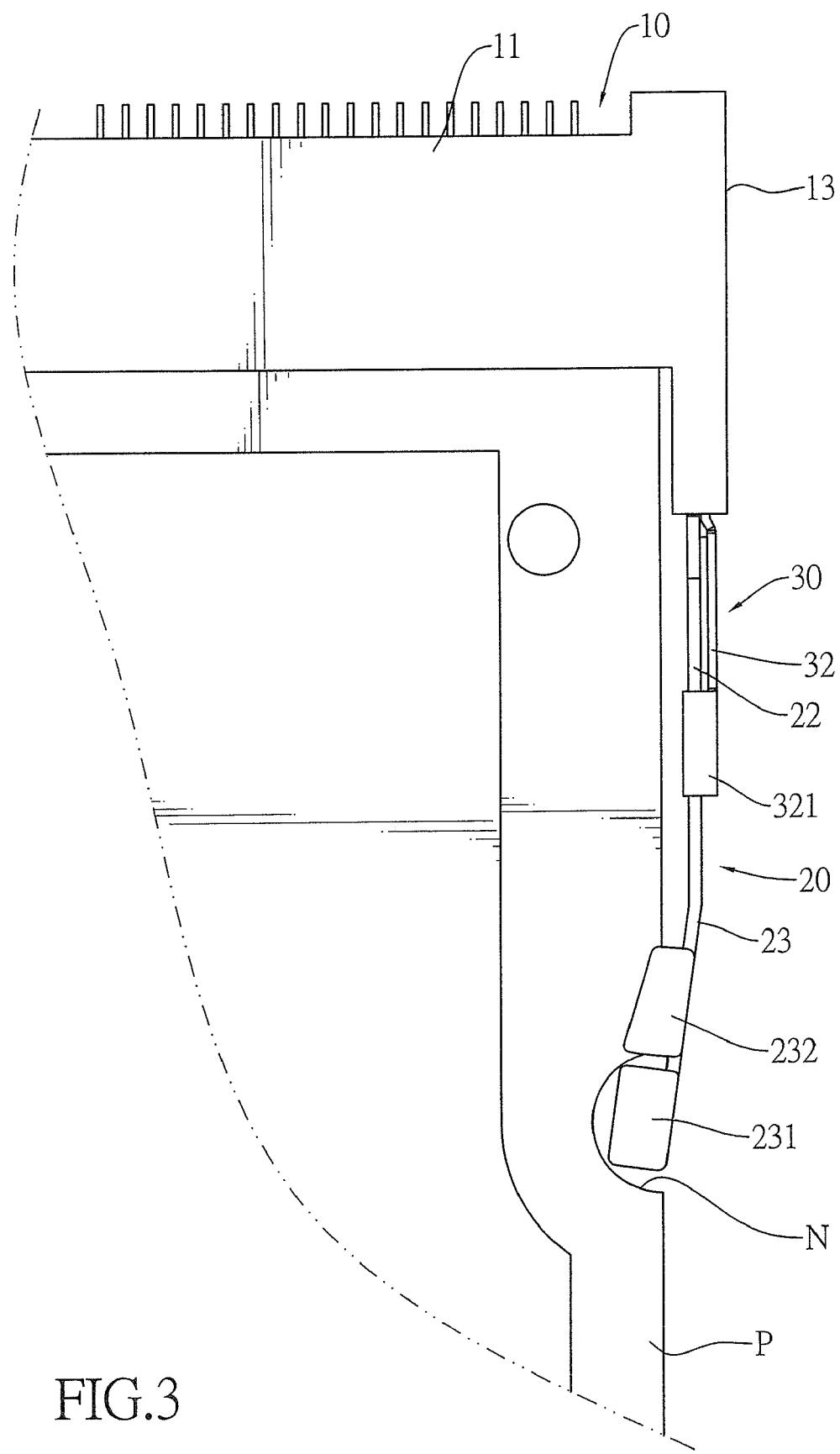
FIG. 3 is an enlarged top view of the electrical connector in FIG. 1 holding a memory module.
Figure 4:
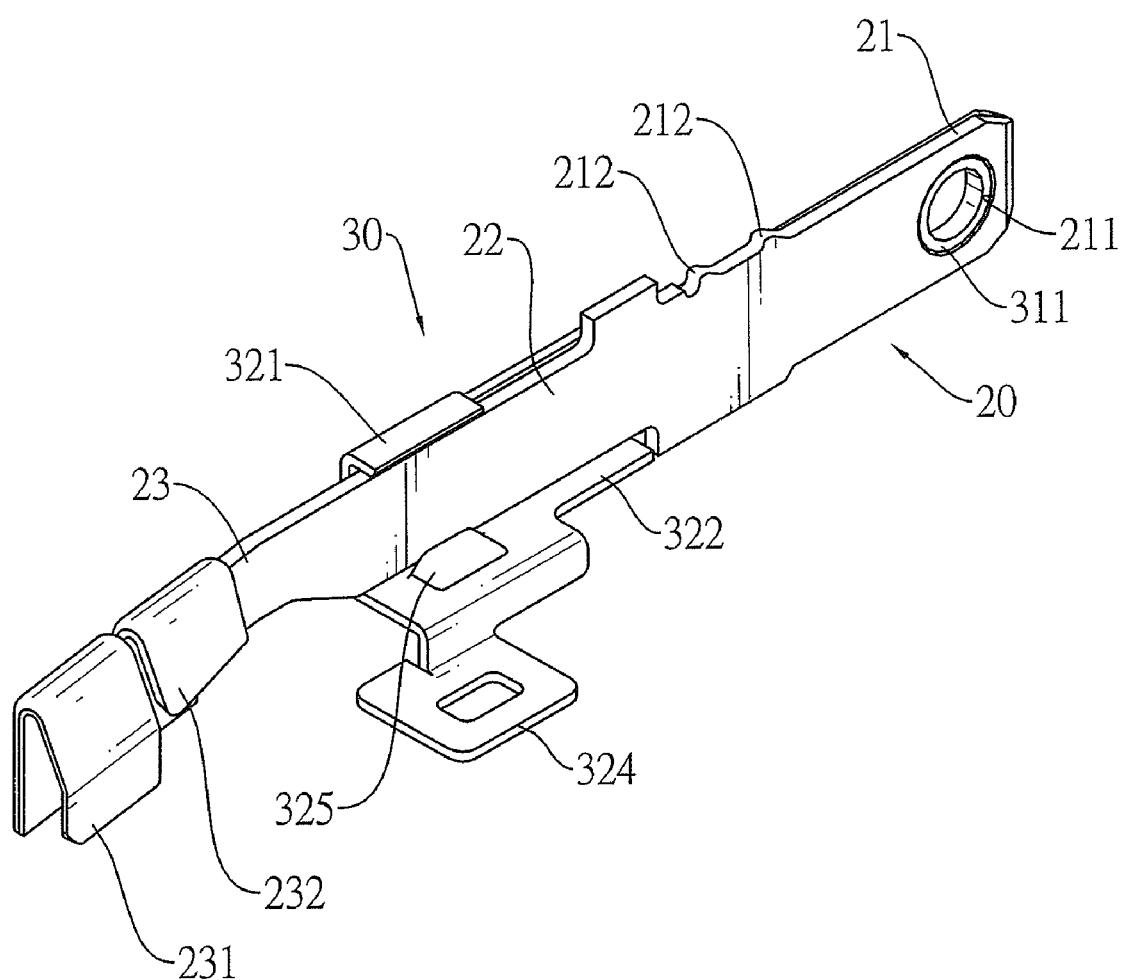
FIG. 4 is a perspective view of a latching member and a bracket of the electrical connector in FIG. 1.
Figure 5:
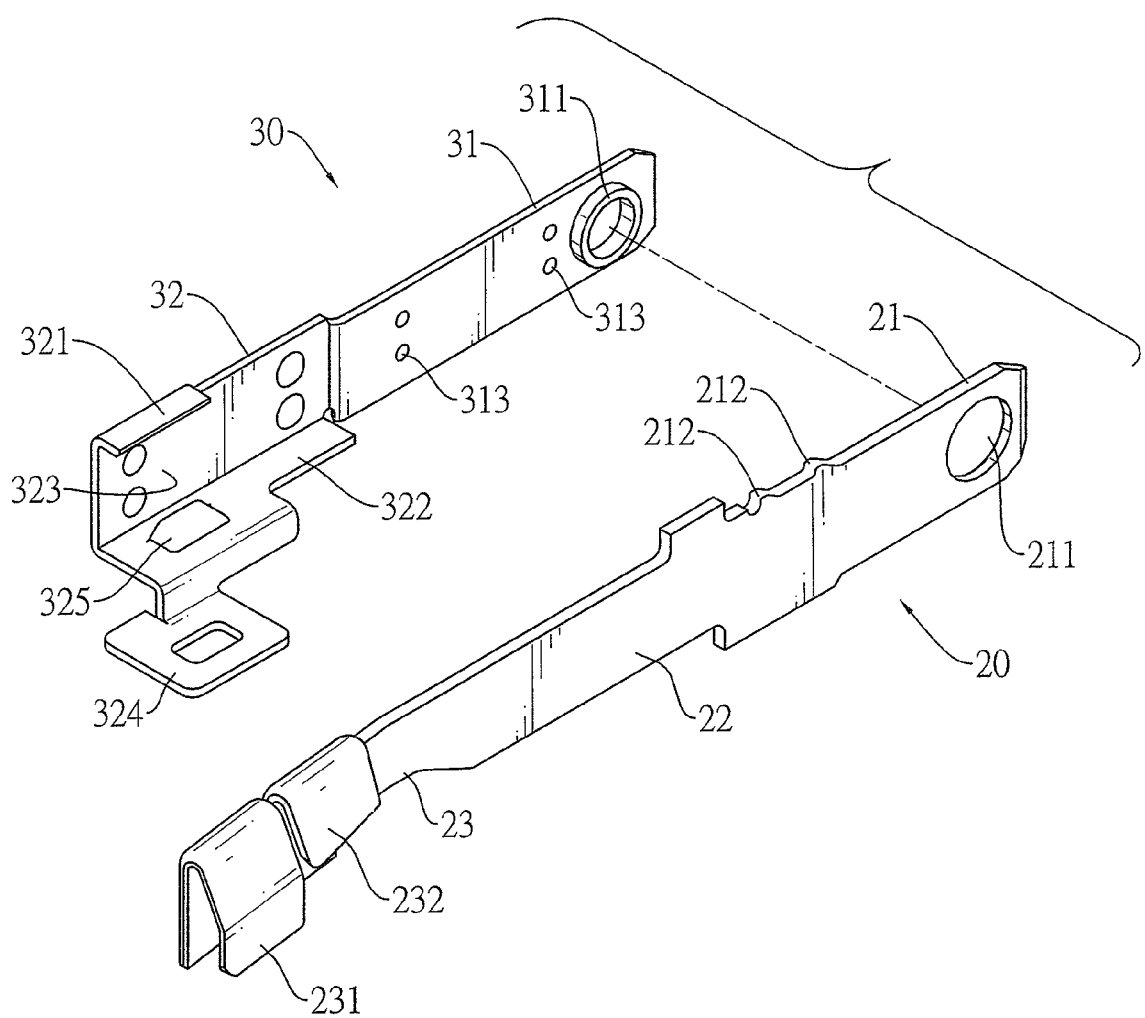
FIG. 5 is an exploded perspective view of the latching member and the bracket of the electrical connector in FIG. 4.
Figure 6:
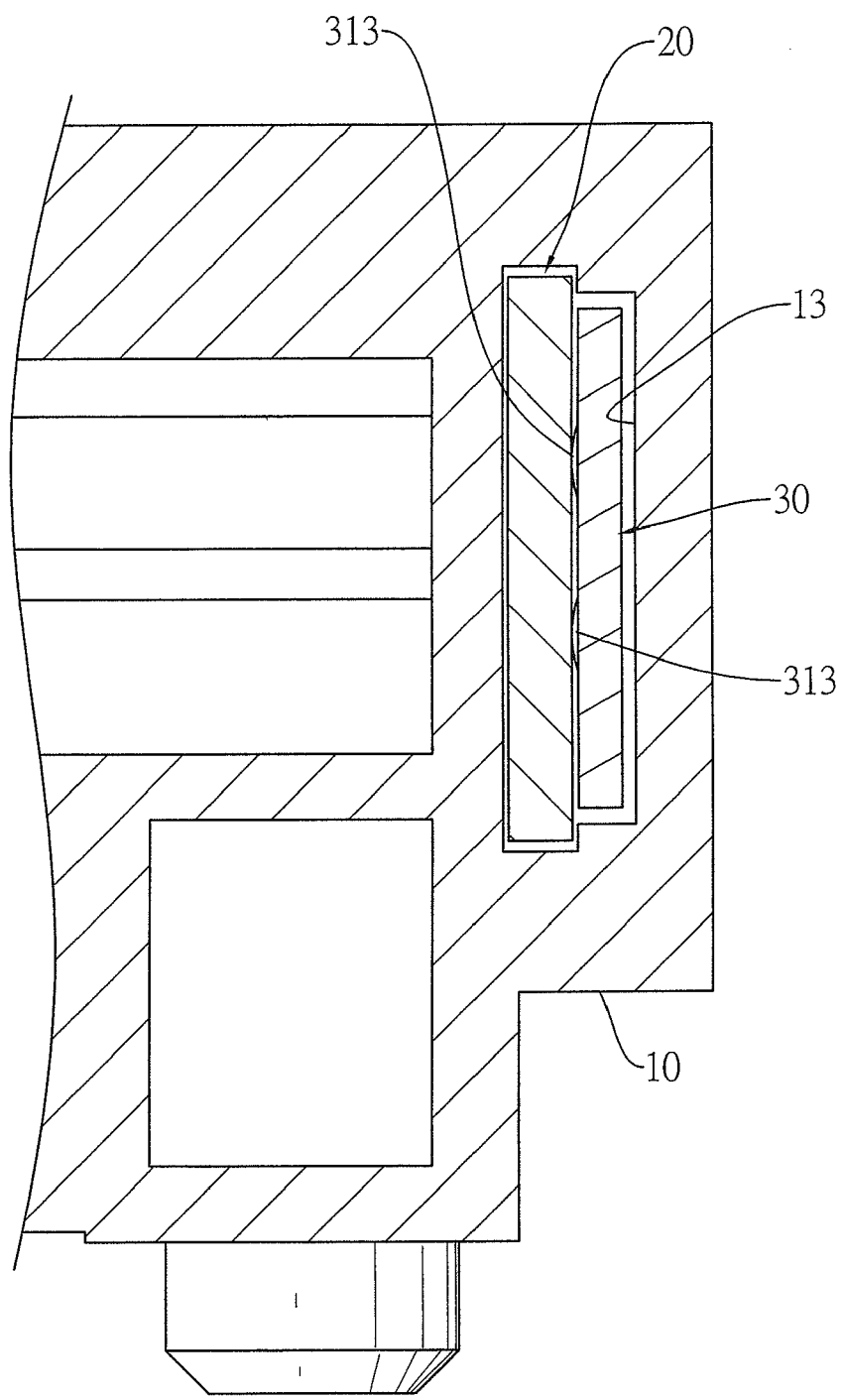
FIG. 6 is a cross sectional front view of the electrical connector in FIG. 1.

With reference to FIGS. 1 to 3, an electrical connector in accordance with the present invention may be a socket connector holding a memory module (P). The memory module (P) may be a dynamic random access memory (DRAM) and has a top surface, two opposite sides and two notches (N) respectively defined in the sides.

The electrical connector comprises an insulative housing (10), a plurality of terminals (40) and two fastening assemblies.

The insulative housing (10) has two opposite sides, a base (11), a tongue (12) and two opposite mounts (13).

The base (11) has a front and two opposite sides.

The tongue (12) is formed on and protrudes forwards from the front of the base (11) and has a plurality of terminal slots (121). The terminal slots (121) are defined in the tongue (12).

The mounts (13) are formed respectively on the sides of the insulative housing (10), may be respectively on sides of the base (11) and each mount (13) has a front end and a mounting hole (131) defined in the front end and having an inner surface.

The terminals (40) are mounted respectively in the terminal slots (121) of the tongue (12).

With further reference to FIGS. 3 to 6, the fastening assemblies correspond respectively to, are mounted respectively in and extend partially out from the mounting holes (131) of the mounts (13) of the insulative housing (10). Each fastening assembly has a latching member (20) and a bracket (30).

The latching member (20) is mounted in a corresponding mounting hole (131) and has a mounting section (21), a positioning section (22), a resilient arm (23) and a hooking section (231) and may further have a limiting section (232).

The mounting section (21) is mounted in the corresponding mounting hole (131) and has a connecting element (211) and teeth (212). The connecting element (211) is formed on the mounting section (21) and may be a through hole defined through the mounting section (21). The teeth (212) are formed on the mounting section (21) and bite the inner surface of the corresponding mounting hole (131) of the mount (13) to improve the combining strength of the latching member (20) with the mount (13).

The positioning section (22) is formed on and protrudes forwards from the mounting section (21).

The resilient arm (23) is formed on and protrudes forwards from the positioning section (22), may be inclined transversely towards the other resilient arm (23) and has a top edge.

The hooking section (231) is formed on and protrudes obliquely downwards from the top edge of the resilient arm (23) and may be engaged with one notch (N) of the memory module (P).

The limiting section (232) is formed on and protrudes obliquely downwards from the top edge of the resilient arm (23) and is shorter than the hooking section (232). When the memory module (P) is engaged with the electrical connector, the limiting section (232) abuts on the top surface of the memory module (P) to prevent the memory module (P) from being pulled out or falling off.

The bracket (30) is mounted movably in the corresponding mounting hole (131) of the mount (13) of the insulative housing (10), is mounted pivotally on the connecting element (211) of the latching member (20) and has a mounting section (31) and a supporting section (32).

The mounting section (31) is mounted movably in the corresponding mounting hole (131), has a pivoting element (311) and may further have bumps (313). The pivoting element (311) is formed on the mounting section (31), is connected pivotally to the connecting element (211) of the latching member (20) and may be a pivot pin mounted through the through hole. The bumps (313) are formed on and protrude transversely from the mounting section (31) and abut the mounting section (21) of the latching member (20) to form an interval between the bracket (30) and the latching member (20). The interval reduces the friction between the bracket (30) and the latching member (20) and facilitates the relative movement of thereof.

The supporting section (32) is formed on and protrudes forwards from the mounting section (31) of the bracket (30), has a top edge, a bottom edge, a top plate (321), a bottom plate (322), a space (323) and a soldering portion (324) and may further have a limiting protrusion (325). The top and bottom plates (321, 322) are formed on and transversely protrude respectively inwards from the top and bottom edges. The space (323) is defined by the supporting section (32) and the top and bottom plates (321, 322) and holds the positioning section (22) of the latching member (20). The soldering section (324) is formed on and protrudes from the bottom edge of the supporting section (32) and may be soldered on a PCB to securely mount the electrical connector on the PCB. The limiting protrusion (325) is formed on and protrudes upwards from the bottom plate (322) and limits the positioning section (22) of the latching member (20) in the space (323) without inadvertently falling off.

Figure 7:
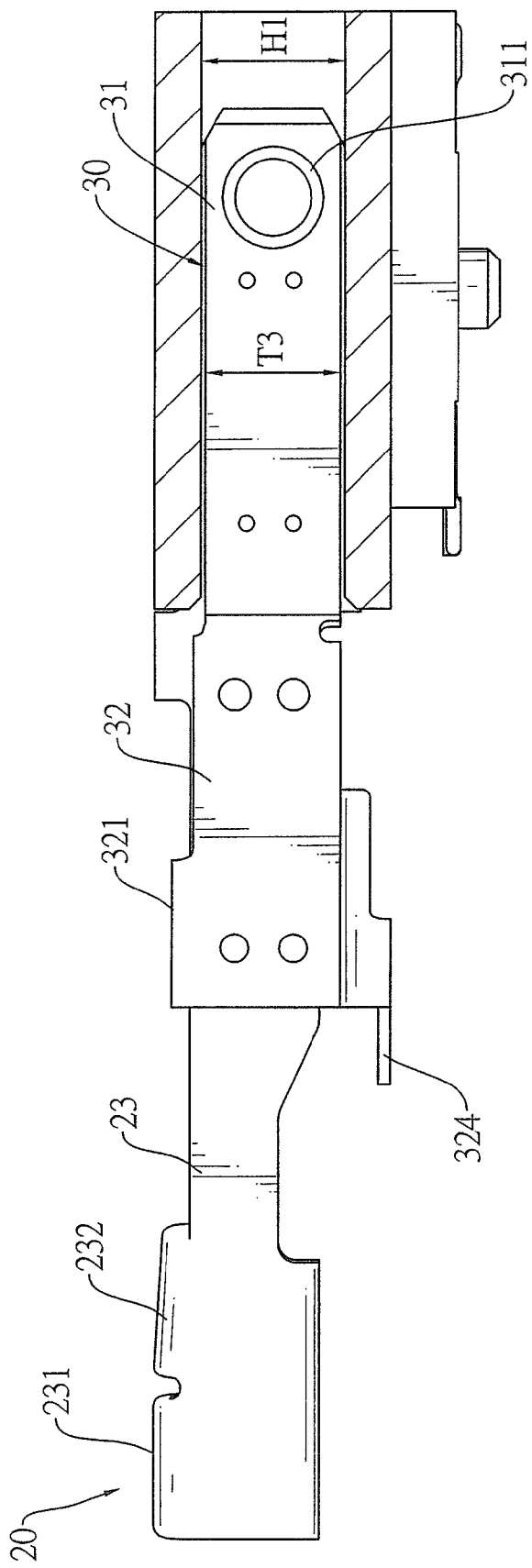
FIG. 7 is a side view in partial section of the electrical connector in FIG. 1.

With further reference to FIG. 7, in a preferred embodiment, the height (H1) of the mounting hole (131) of each mount (13) is larger than the vertical thickness (T3) of the mounting section (31) of each bracket (30). Therefore, the mounting section (31) of each bracket (30) may pivot vertically in the corresponding mounting hole (131).

Figure 8:
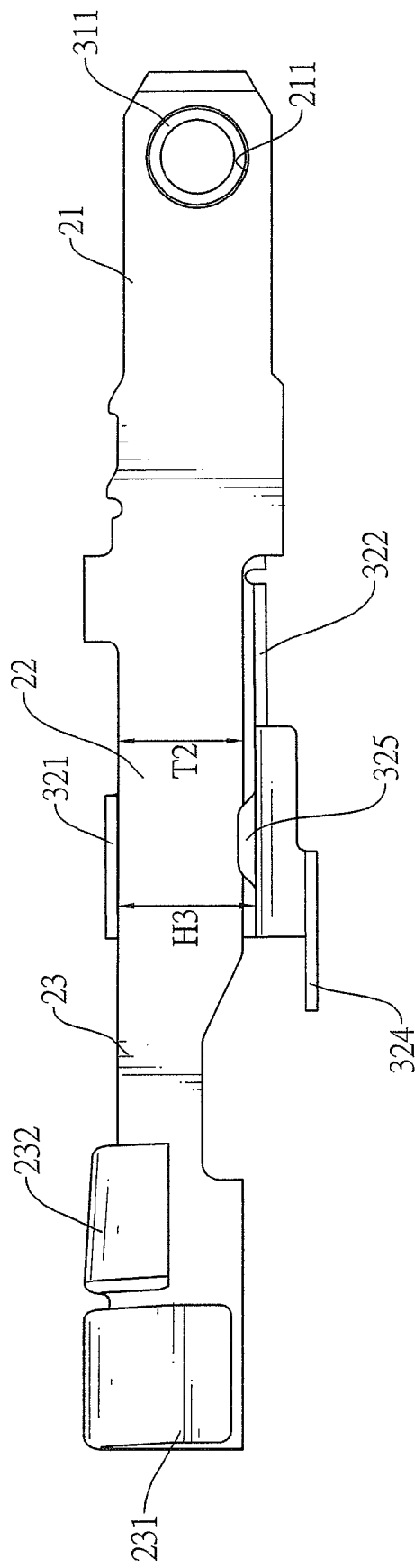
FIG. 8 is an operational side view of the resilient member lifting slightly up in the bracket of the electrical connector in FIG. 1.
Figure 9:
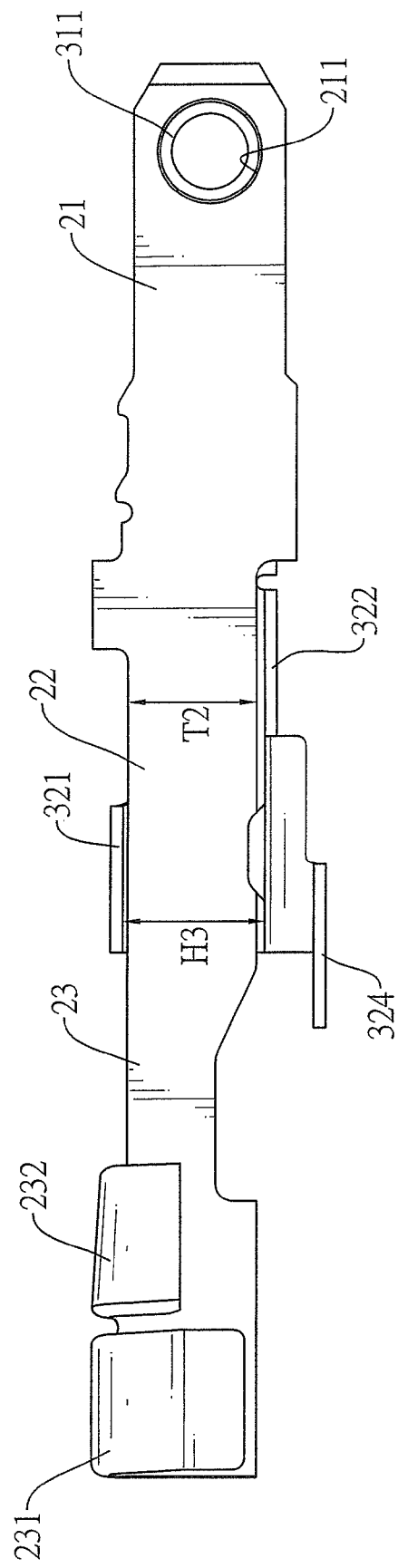
FIG. 9 is another operational side view of the resilient member pivoting down in the bracket of the electrical connector in FIG. 8.

With further reference to FIGS. 8 and 9, in a preferred embodiment, the height (H3) of the space (323) of each bracket (30) is larger than the vertical thickness (T2) of the positioning section (22) of each latching member (20). Therefore, the positioning section (22) of each latching member (20) may be move up and down in a corresponding space (323).

Furthermore, in a preferred embodiment, the outer diameter of the pivot pin of each bracket (30) is smaller than the inner diameter of the through hole of each latching member (20). Therefore, each bracket (30) pivots loosely on a corresponding latching member (20) to make the electrical connector more flexible to adapt different PCBs with different tolerances.

Because the mounting sections (31) of the brackets (30) are mounted movably on the mounting holes (131) of the insulative housing (10) and are connected pivotally to the mounting sections (21) of the latching members (20), the brackets (30) slightly float on the latching members (20). Therefore, even though the insulative housing (10) is mounted unevenly on a PCB, the bracket (30) may slightly pivot up or down to successfully contact the PCB to facilitate the soldering of the soldering section (324) on the PCB. The electrical connector is deemed to have a higher tolerance relative to different PCBs and memory module and advantages the fabrication of the electrical connector on PCBs.

Even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An electrical connector comprising:
    an insulative housing having two sides and two mounts formed respectively on the sides and each mount having a front end and a mounting hole defined in the front end and having an inner surface;
    a plurality of terminals mounted on the insulative housing; and
    two fastening assemblies corresponding respectively to, mounted respectively in and extending partially out from the mounting holes of the mounts of the insulative housing and each fastening assembly having
        a latching member mounted in a corresponding mounting hole and having
            a mounting section mounted in the corresponding mounting hole and having a connecting element formed on the mounting section;
            a positioning section formed on and protruding forwards from the mounting section;
            a resilient arm formed on and protruding forwards from the positioning section; and
            a hooking section formed on and protruding from the resilient arm; and
        a bracket mounted movably in the corresponding mounting hole of the mount of the insulative housing, mounted pivotally on the connecting element of the latching member and having
            a mounting section mounted movably in the corresponding mounting hole and having a pivot element formed on the mounting section and connected pivotally to the connecting element of the latching member; and
            a supporting section formed on and protruding forwards from the mounting section of the bracket and having
                a top edge;
                a bottom edge;
                a top plate formed on and protruding transversely inwards from the top edge;
                a bottom plate formed on and protruding transversely inwards from the bottom edge;

a space defined by the supporting section and the top and bottom plates and holding the positioning section of the latching member; and a soldering portion formed on and protruding from the bottom edge of the supporting section.

2. The electrical connector as claimed in claim 1 further comprising the height of the space each bracket is larger than the vertical thickness of the positioning section of each latching member.

3. The electrical connector as claimed in claim 2, wherein the height of the mounting hole of each mount is larger than the vertical thickness of the mounting section of each bracket.

4. The electrical connector as claimed in claim 3, wherein the connecting element of the mounting section of each latching member is a through hole defined through the mounting section; and the pivot element of the mounting section of each bracket is a pivot pin mounted through the through hole of one latching member.

5. The electrical connector as claimed in claim 4, wherein the outer diameter of the pivot pin of each bracket is smaller than the inner diameter of the through hole of each latching member.

6. The electrical connector as claimed in claim 5, wherein the mounting section of each bracket further has bumps formed on and protruding transversely from the mounting section and abutting the mounting section of one latching member.

7. The electrical connector as claimed in claim 6, wherein the resilient arm of each latching member is inclined transversely towards the other resilient arm.

8. The electrical connector as claimed in claim 7, wherein the mounting section of each latching member further has teeth formed on the mounting section and biting the inner surface of the corresponding mounting hole.

9. The electrical connector as claimed in claim 8, wherein each latching member further has a limiting section formed on the resilient arm and shorter than each hooking section.

10. The electrical connector as claimed in claim 9, wherein the supporting section of each bracket further has a limiting protrusion formed on and protruding upwards from the bottom plate and limiting the positioning section of one latching member in the space.

11. The electrical connector as claimed in claim 10, wherein the insulative housing further has
a base formed having two opposite sides; and
a tongue formed on and protruding from the base;
the terminals are mounted on the tongue; and
the mounts are formed respectively on the sides of the base.

\* \* \* \* \*